(12) United States Patent
Kim et al.

(10) Patent No.: US 10,112,461 B2
(45) Date of Patent: Oct. 30, 2018

(54) PHOTOCATALYST DEVICE AND AIR CONDITIONER FOR VEHICLE HAVING THE SAME

(71) Applicants: HANON SYSTEMS, Daejeon-si (KR); ESKO CO., LTD., Gyeongsangnam-do (KR)

(72) Inventors: Jae-Ho Kim, Daejeon-si (KR); Ji-Yong Park, Daejeon-si (KR); Youn-Woo Lim, Daejeon-si (KR); Yong-Jun Jee, Daejeon-si (KR); Gi-Woo Ro, Daejeon-si (KR); Jun-Seong Ahn, Daejeon-si (KR)

(73) Assignee: HANON SYSTEMS, Daejeon (KR)

(*) Notice: Subject to any disclaimer, the term of this patent is extended or adjusted under 35 U.S.C. 154(b) by 104 days.

(21) Appl. No.: 14/907,606

(22) PCT Filed: Jan. 21, 2015

(86) PCT No.: PCT/KR2015/000625
§ 371 (c)(1),
(2) Date: Jan. 26, 2016

(87) PCT Pub. No.: WO2015/111911
PCT Pub. Date: Jul. 30, 2015

(65) Prior Publication Data
US 2016/0325606 A1 Nov. 10, 2016

(30) Foreign Application Priority Data

Jan. 22, 2014 (KR) .................. 10-2014-0007513
Sep. 24, 2014 (KR) .................. 10-2014-0127617
Sep. 26, 2014 (KR) .................. 10-2014-0128992

(51) Int. Cl.
*A61L 9/20* (2006.01)
*B60H 3/06* (2006.01)
(Continued)

(52) U.S. Cl.
CPC ............ *B60H 3/0608* (2013.01); *A61L 9/205* (2013.01); *B60H 1/00521* (2013.01); *B60H 1/12* (2013.01);
(Continued)

(58) Field of Classification Search
CPC .............................. A61L 9/205; B60H 3/0608
(Continued)

(56) References Cited

U.S. PATENT DOCUMENTS

2012/0180998 A1  7/2012  Nishioka et al.

FOREIGN PATENT DOCUMENTS

JP       63005581     1/1988
JP       11-198640 A  7/1999
(Continued)

OTHER PUBLICATIONS

English Translation of Foreign Document No. KR100945599 provided by espacenet.com: Kim Kyung Soo, Hybrid Optical Semiconductor Sterilization Catalyst Lamp and Optical Catalyst Purification Device Using the Same, Mar. 4, 2010 (Year: 2010).*

*Primary Examiner* — Kevin Joyner
(74) *Attorney, Agent, or Firm* — Shumaker, Loop & Kendrick, LLP; James D. Miller

(57) ABSTRACT

The present invention relates to a photocatalyst device including: a body; a light source part fixed to the body to irradiate ultraviolet light and having an LED and a substrate for fixing the LED thereto; a catalyst part fixed to the body to conduct photocatalytic reaction with the light irradiated by the light source part and thus to generate superoxygen radicals; and a heat radiating part disposed on the light source part to radiate the heat generated from the light source part, whereby the photocatalyst device purifies air and sterilizes and deodorizes the evaporator, while being easily mountable as a single module.

12 Claims, 10 Drawing Sheets

(51) Int. Cl.
 *B60H 1/00* (2006.01)
 *B60H 1/12* (2006.01)
 *B60H 1/32* (2006.01)

(52) U.S. Cl.
 CPC ........ *B60H 1/3204* (2013.01); *A61L 2209/12* (2013.01); *A61L 2209/16* (2013.01); *B60H 2003/0675* (2013.01)

(58) Field of Classification Search
 USPC ........................................................ 422/122
 See application file for complete search history.

(56) References Cited

FOREIGN PATENT DOCUMENTS

| | | | |
|---|---|---|---|
| JP | 2000129595 | A | 5/2000 |
| JP | 2002360678 | A | 12/2002 |
| JP | 2004135851 | A | 5/2004 |
| JP | 2004267947 | A | 9/2004 |
| JP | 2009293209 | A | 12/2009 |
| JP | 2009295578 | A | 12/2009 |
| JP | 2010149536 | A | 7/2010 |
| JP | 2012158320 | A | 8/2012 |
| KR | 1020010035747 | A | 5/2001 |
| KR | 1020030012608 | A | 2/2003 |
| KR | 10-0945599 | B1 | 3/2010 |
| KR | 100945599 | B1 | 3/2010 |
| WO | 2008132817 | A1 | 11/2008 |

\* cited by examiner

PHOTOCATALYST DEVICE AND AIR CONDITIONER FOR VEHICLE HAVING THE SAME

CROSS-REFERENCES TO RELATED APPLICATIONS

This patent application is a United States national phase patent application based on PCT/KR2015/000625 filed on Jan. 21, 2015, which claims the benefit of Korean Patent Application No. 10-2014-0007513 filed on Jan. 22, 2014, Korean Patent Application No. 10-2014-0127617 filed on Sep. 24, 2014, and Korean Patent Application No. 10-2014-0128992 filed on Sep. 26, 2014. The disclosures of the above patent applications are hereby incorporated herein by reference in their entirety.

BACKGROUND OF THE INVENTION

Field of the Invention

The present invention relates to a photocatalyst device and an air conditioner for a vehicle having the same, and more particularly, to a photocatalyst device and an air conditioner for a vehicle having the same that purifies the air introduced into an air conditioner case, sterilizes and deodorizes an evaporator, and effectively radiates the heat generated from the photocatalyst device, thus continuously keeping the sterilization and deodorization performance.

Background of the Related Art

An air conditioner for a vehicle is a device that heats and cools air in the process of introducing external air into the vehicle or circulating internal air into the vehicle to conduct the heating or cooling in the interior of the vehicle. The air conditioner includes an evaporator disposed inside an air conditioner case to perform cooling and a heater core disposed inside the air conditioner to perform heating, so that the cool air by the evaporator and the heated air by the heater core are selectively blown into respective portions of the interior of the vehicle by means of a blowing mode switching door.

With the increment of a vehicle supply rate, on the other hand, the time during which passengers stay in the vehicle is extended, and accordingly, many studies have been made to maintain the freshness of air in the interior of the vehicle. However, the internal space of the vehicle is relatively small and closed and also easy to be polluted, and due to fine dust and various pollutants in cities, further, air pollution in the interior of the vehicle becomes more serious. As a result, air conditioners for a vehicle have been recently developed to purify the internal air of the vehicle.

One example of conventional air conditioners for a vehicle is disclosed in Japanese Patent No. 2549032 (issued on May 30, 1997) entitled 'cooling device for vehicle to which deodorizer is attached'. FIG. 1 is a sectional view showing the conventional cooling device for a vehicle to which a deodorizer is attached.

As shown in FIG. 1, the conventional cooling device for a vehicle, to which a deodorizer is attached, has a body 20 having an external air inlet 21 and an internal air inlet 22 and an intake door 23 rotatably mounted to selectively open and close the external air inlet 21 and the internal air inlet 22. An actuator 30 is connected to a rotary shaft of the intake door 23 and controlled by control means 31. Further, a blower 25 is located behind the intake door 23 to blow the air introduced from the external air inlet 21 and the internal air inlet 22 into downstream side, and the blower 25 includes a fan 32 and a motor 33 for rotating the fan 32. An evaporator 26 is located behind the blower 25 to perform the heat exchange with the air passing therethrough, thus achieving air cooling. Further, a photocatalyst filter 27 is located on an air passage 28 behind the evaporator 26 to produce reactive oxygen through the irradiation of light having long wavelength. The photocatalyst filter 27 produces the reactive oxygen through the irradiation of an ultraviolet lamp 29, and the reactive oxygen oxidizes and decomposes the materials causing bad odor into extremely low-concentration oxidized compounds. The ultraviolet lamp 29 is located between the evaporator 26 and the photocatalyst filter 27. Moreover, a metal catalyst filter 34 is located behind the photocatalyst filter 27 to remove ozone contained in the flowing air. A reference numeral 35 indicates a temperature sensor, a reference numeral 36 a sensor for sensing bad odor levels, a reference numeral 37 a fan switch, and a reference numeral 24 an air outlet.

According to the conventional cooling device, however, the ultraviolet lamp 29 used as a light source of the photocatalyst contains mercury harmful to the human body thereinto, and due to bad environmental reasons, accordingly, the conventional cooling device is not actually applicable to the vehicle. Further, the photocatalyst filter 27 is located behind the evaporator 26 and thus absorbs and deodorizes the bad odor generated from the evaporator 26, so that when an amount of dust is excessively large to decrease an air-flow rate, the photocatalyst filter 27 should be exchanged with new one. According to the conventional cooling device, in addition, the ultraviolet lamp 29 and the photocatalyst filter 27 are provided as individual parts, thus making the assembly performance of the device deteriorated.

SUMMARY OF THE INVENTION

Accordingly, the present invention has been made in view of the above-mentioned problems occurring in the prior art, and it is an object of the present invention to provide a photocatalyst device and an air conditioner for a vehicle having the same that purifies the air introduced into an air conditioner case, sterilizes and deodorizes an evaporator, and effectively radiates the heat generated from the photocatalyst device, thus continuously keeping the sterilization and deodorization performance.

To accomplish the above-mentioned object, according to a first aspect of the present invention, there is provided a photocatalyst device including: a body; a light source part fixed to the body to irradiate ultraviolet light and having an LED and a substrate for fixing the LED thereto; a catalyst part fixed to the body to conduct photocatalytic reaction with the light irradiated by the light source part and thus to generate superoxygen radicals; and a heat radiating part disposed on the light source part to radiate the heat generated from the light source part, whereby the photocatalyst device purifies air and sterilizes and deodorizes the evaporator, while being easily mountable as a single module.

According to the present invention, preferably, the body includes: a support portion for supporting the substrate of the light source part; a space-forming portion extended from the support portion to form a given distance between the LED of the light source part and the catalyst part; and a catalyst part-accommodating portion extended from the space-forming portion to fix the catalyst part thereto, the space-forming portion being inclinedly increased in width from the support portion toward a light irradiation direction of the light source part, so that the other parts (the light source part, the catalyst part and the heat radiating part) are supported by the body, thus making the photocatalyst device as a single module.

According to the present invention, preferably, the body has drain holes formed thereon to drain water therefrom, and at this time, the drain holes are formed on the slant lower side of the space-forming portion in the state where the photocatalyst device is mounted, thus preventing the durability of the photocatalyst device from being decreased due to the water introduced into the photocatalyst device.

According to the present invention, preferably, the substrate whose surface facing the catalyst part is coated with a water-proofing material, thus in advance preventing the substrate from being damaged due to water.

According to the present invention, preferably, the heat radiating part includes a first radiating fin member located on one side of the substrate in such a manner as to protrude toward the catalyst part, and at this time, the first radiating fin member is formed on the entire area of the light source part except the area on which light is irradiated from the LED to the catalyst part, while having a shape of a plate disposed in parallel to an air flow direction, so that the heat generated from the LED can be effectively radiated, while preventing the interference in the irradiation of the light of the LED to the catalyst part.

According to the present invention, preferably, the heat radiating part includes a second radiating fin member disposed on the opposite side of the substrate on which the LED is located, so as to effectively radiate the heat generated from the photocatalyst device.

According to the present invention, preferably, the substrate itself is the heat radiating part as a heat radiating substrate.

According to the present invention, preferably, the catalyst part includes a earner and a coating layer for coating a catalyst liquefied to a form of a gel through addition of promoter and acid additive onto the carrier to allow the catalyst to be carried to the carrier.

According to the present invention, preferably, the catalyst includes titanium oxide having a particle size between 10 nm and 60 nm, and the surface value of the titanium oxide $TiO_2$ is more than 330 $m^2/g$.

According to the present invention, preferably, the promoter is alumina.

According to the present invention, preferably, one catalyst part with one and two or more light source parts are provided, thus performing the sterilization over a relatively large area.

To accomplish the above-mentioned object, according to a second aspect of the present invention, there is provided an air conditioner for a vehicle, including: an air conditioner case for forming a space in which introduced air is conveyed and having vents for discharging the air; an evaporator disposed inside the air conditioner case; a heater core disposed behind the air conditioner case in an air flow direction; and a photocatalyst device having a body, a light source part fixed to the body to irradiate ultraviolet light and having an LED and a substrate for fixing the LED thereto, a catalyst part fixed to the body to conduct photocatalytic reaction with the light irradiated by the light source part and thus to generate superoxygen radicals, and a heat radiating part disposed on the light source part to radiate the heat generated from the light source part, whereby the air introduced into the air conditioner case is purified.

According to the present invention, preferably, the photocatalyst device is located in front of the evaporator in the air flow direction, thus purifying air and sterilizing and deodorizing the evaporator.

According to the present invention, preferably, the air conditioner case has mounting holes hollowed at given areas thereof in such a manner as to be closed by the body, and the body of the photocatalyst device has the fixed portions to the air conditioner case, so that since the photocatalyst device is mounted on one side of the air conditioner case, it can be easily detachably mounted on the air conditioner, thus conducting easy checking and repair and minimizing the interference in the air flow in the interior of the air conditioner case caused by the photocatalyst device.

According to the present invention, preferably, each fixed portion protrudes from the side of the space-forming portion on which the support portion is formed, so that the catalyst part is located at the inside of the air conditioner case and the space-forming portion is located at the outside of the air conditioner case with respect to the external surface of the air conditioner case, thus minimizing the change of air flow in the air conditioner case and the interference in the air flow in the air conditioner case, and the area of the space-forming portion on which drain holes are formed is located on the outside of the area on which the air conditioner case is located, thus easily discharging the water in the photocatalyst device to the outside of the air conditioner case.

BRIEF DESCRIPTION OF THE DRAWINGS

The above and other objects, features and advantages of the present invention will be apparent from the following detailed description of the preferred embodiments of the invention in conjunction with the accompanying drawings, in which.

*Explanation of Reference Numerals

Figure 1:
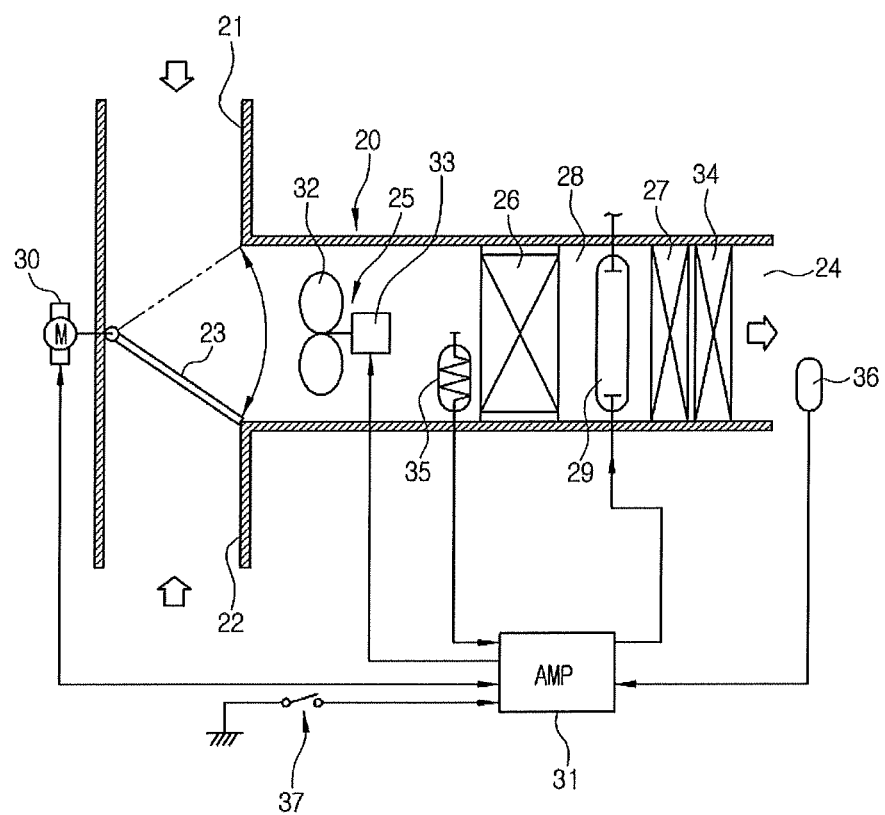
FIG. 1 is a sectional view showing a conventional cooling device for a vehicle to which a deodorizer is attached.

100: photocatalyst device
110: body
111: fixed portion
112: support portion                 112a: hollow portion
113: space-forming portion           113a: drain hole

*Explanation of Reference Numerals

114: catalyst part-accommodating portion
114a: stepped protrusion
120: light source part
121: LED
122: substrate
130: catalyst part
141: first radiating fin member
142: second radiating fin member
131: carrier
132: coating layer
200: blower
211: internal air inlet
212: external air inlet
213: internal and external air switching door
214: fan
300: air conditioner case
300a: mounting hole
310: vent
310d: mode door
320: temperature control door
410: evaporator
420: heater core
500: fastening means
1000: air conditioner for vehicle

DETAILED DESCRIPTION OF THE PREFERRED EMBODIMENTS

Hereinafter, an explanation on a photocatalyst device and an air conditioner for a vehicle having the same according to the present invention will be in detail given with reference to the attached drawing.

Figure 2:
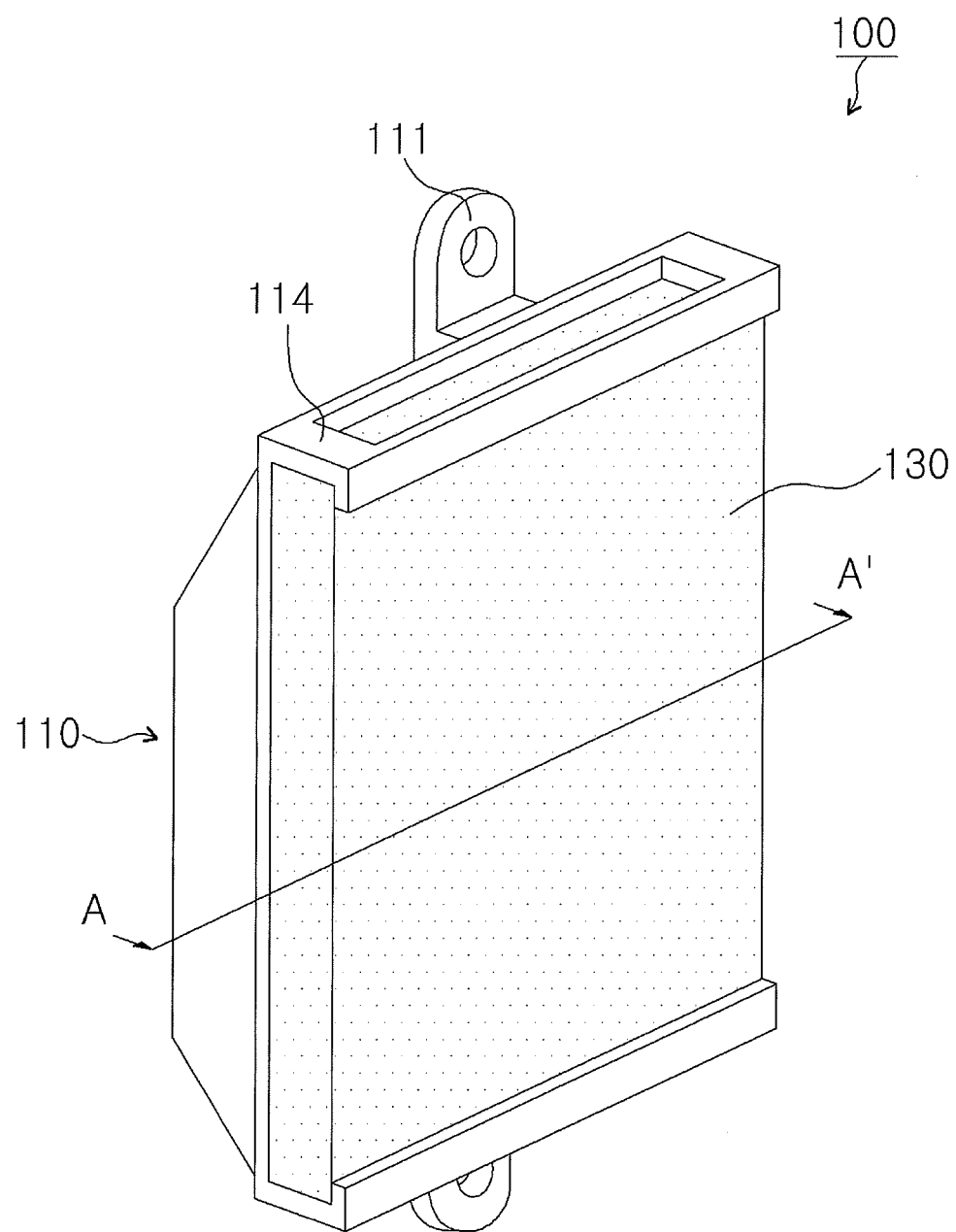
FIGS. 2 and 3 are perspective and sectional views showing a photocatalyst device according to a first embodiment of the present invention.
Figure 3:
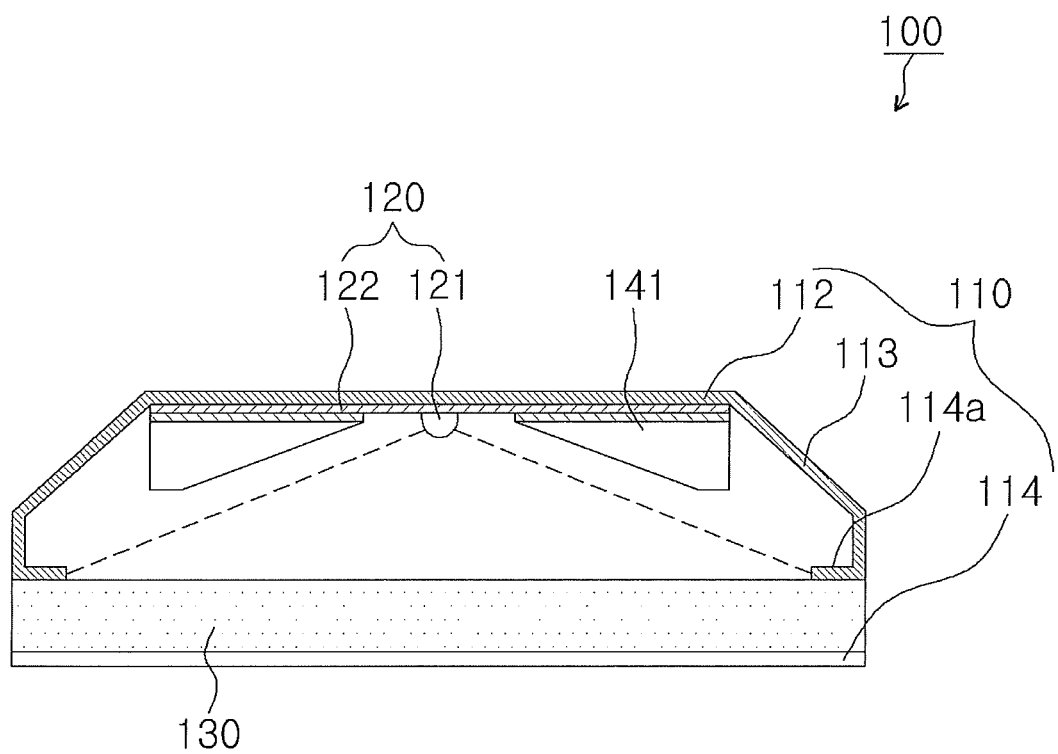
Figure 4:
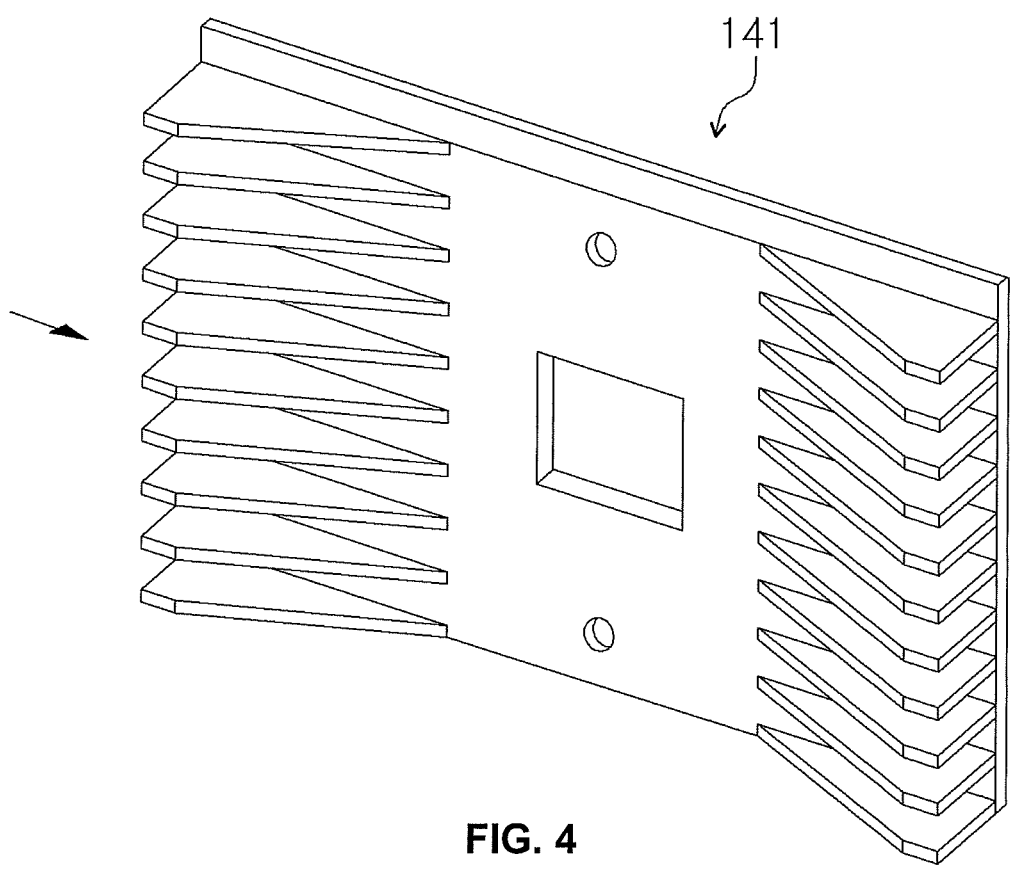
FIG. 4 is a perspective view showing a first radiating fin member of the photocatalyst device according to the first embodiment of the present invention.
Figure 5:
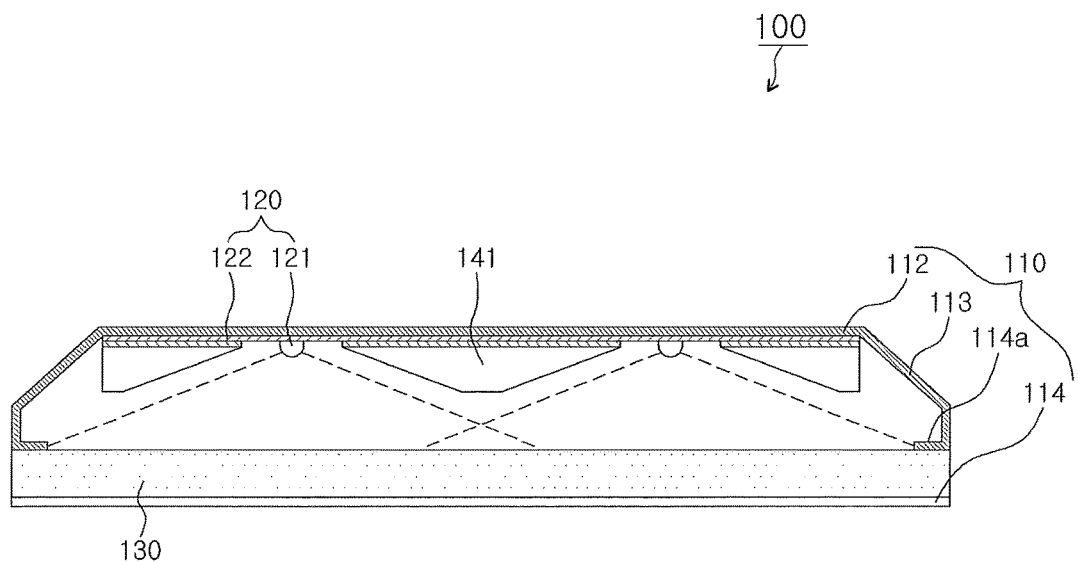
FIGS. 5 and 6 are sectional and perspective views showing a photocatalyst device according to a second embodiment of the present invention and a first radiating fin member of the photocatalyst device.
Figure 6:
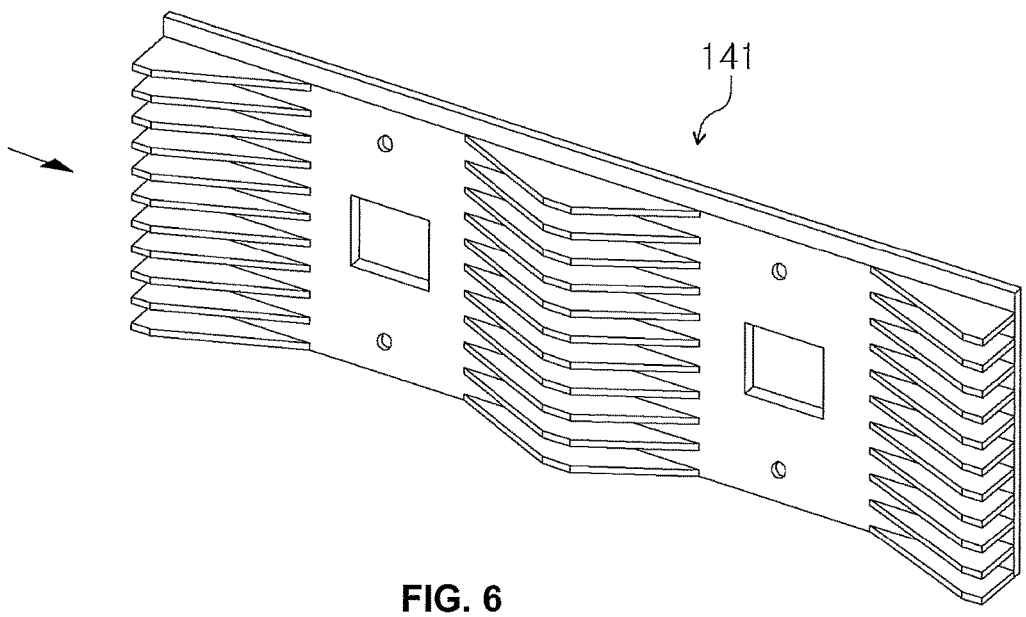
Figure 7:
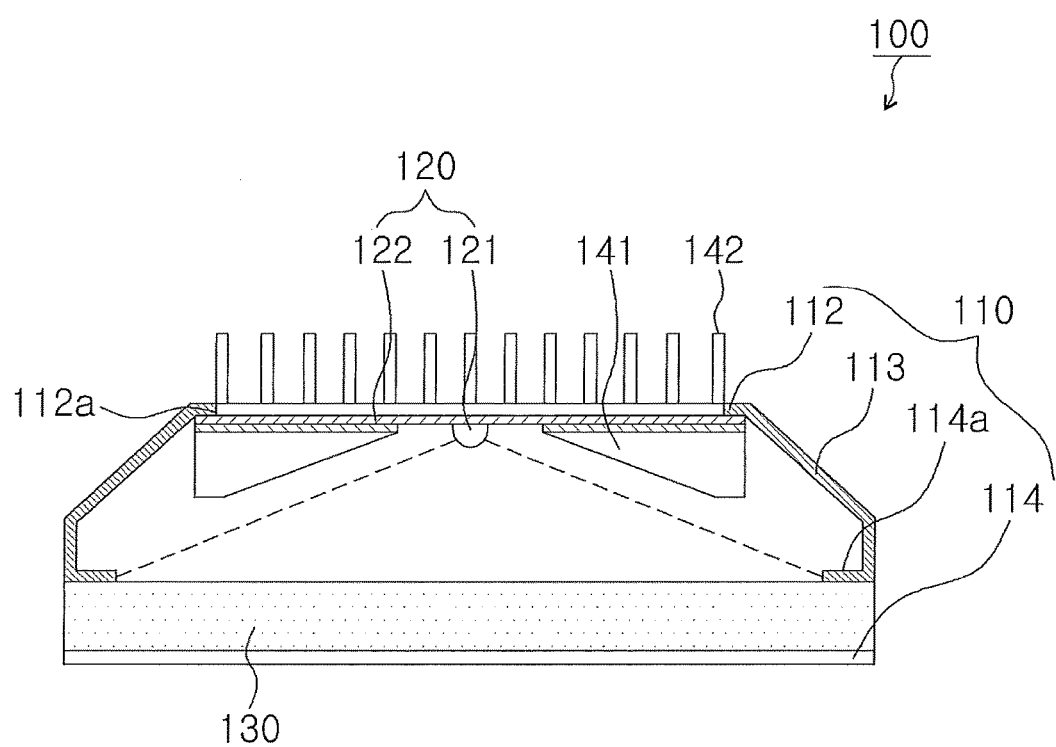
FIG. 7 is a sectional view showing a photocatalyst device according to a third embodiment of the present invention.
Figure 8:
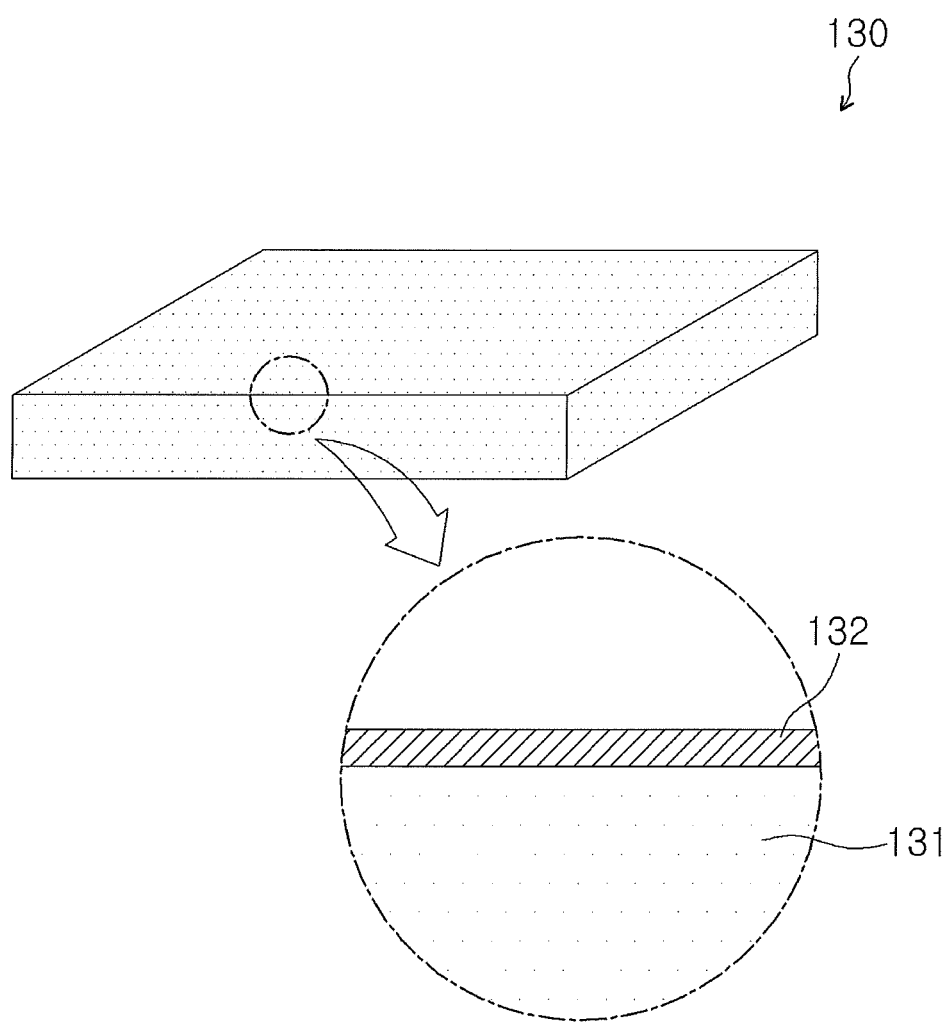
FIG. 8 is an enlarged perspective view showing a catalyst part of the photocatalyst device according to the present invention.
Figure 9:
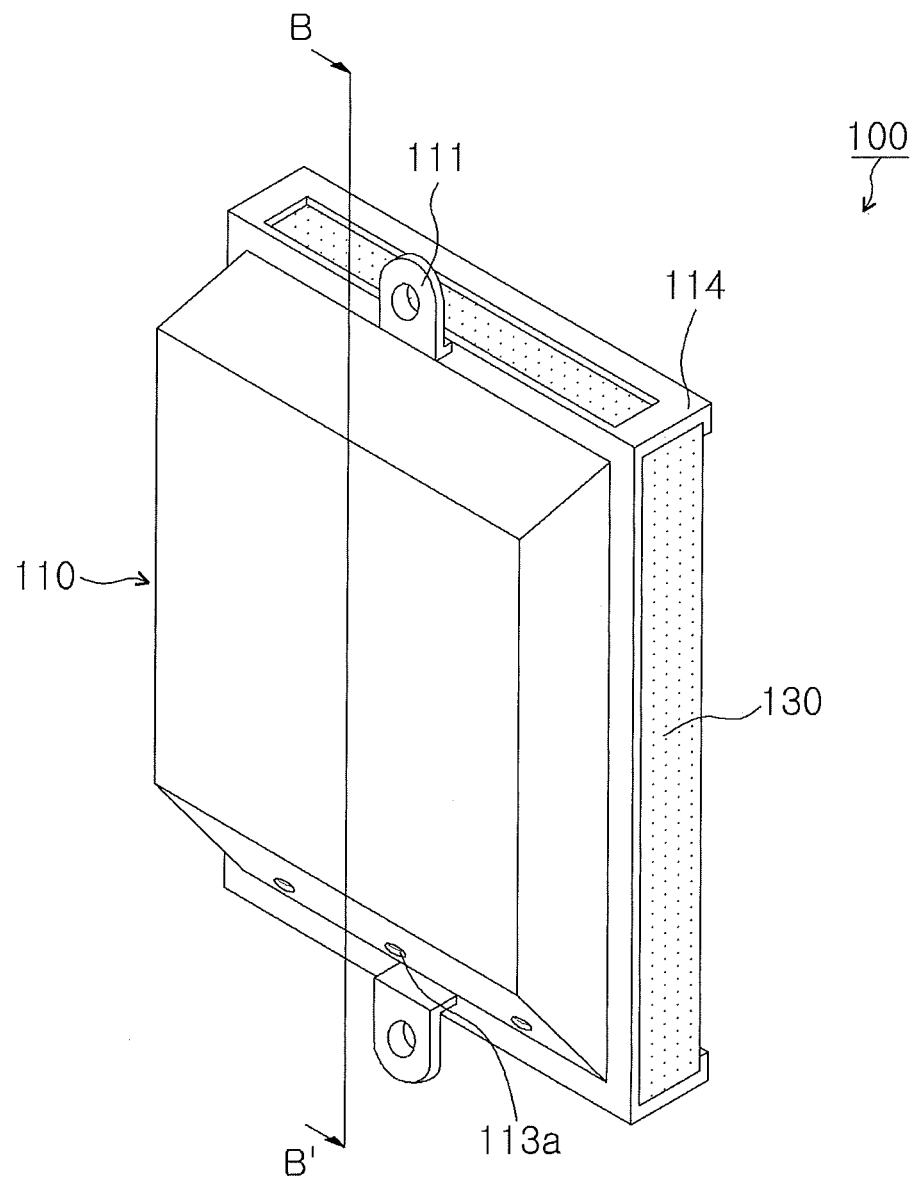
FIGS. 9 and 10 are perspective and sectional views showing a photocatalyst device according to a fourth embodiment of the present invention.
Figure 10:
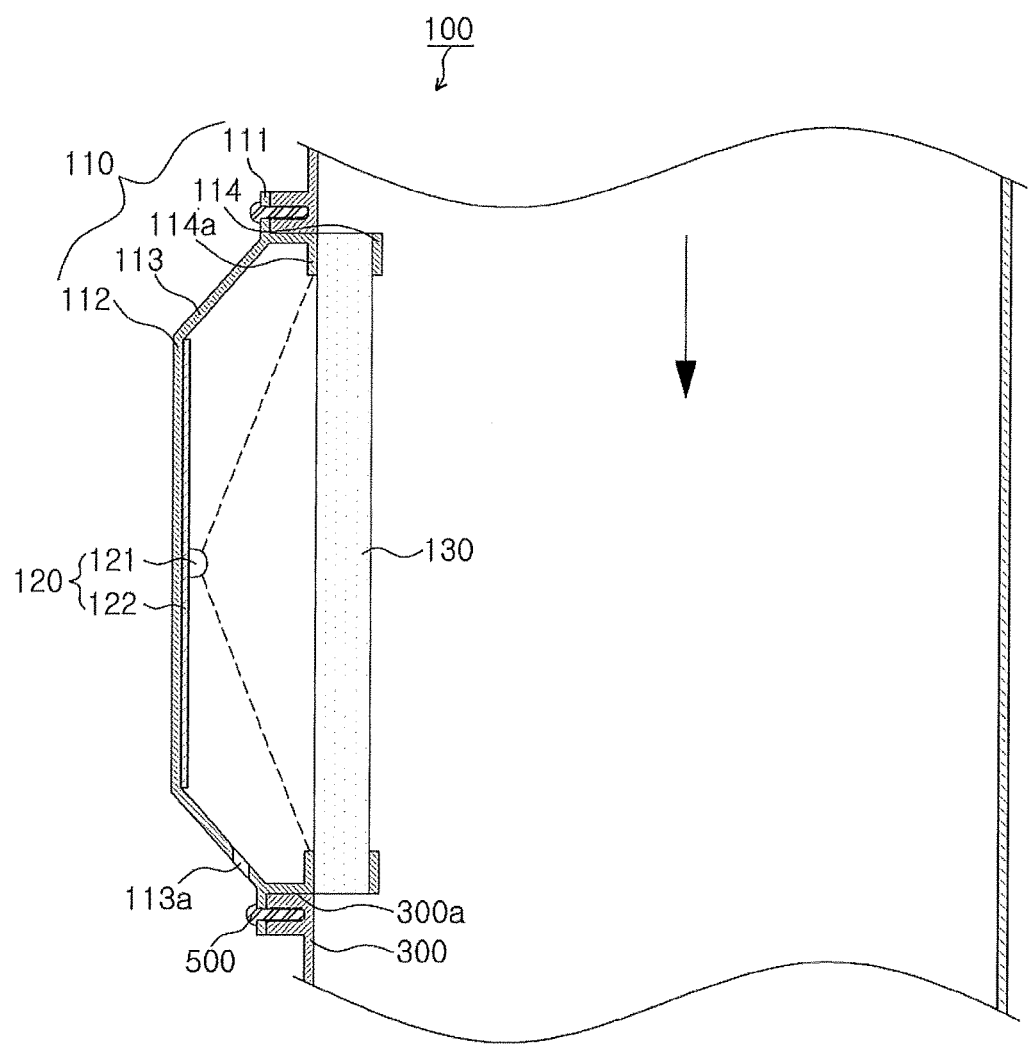
Figure 11:
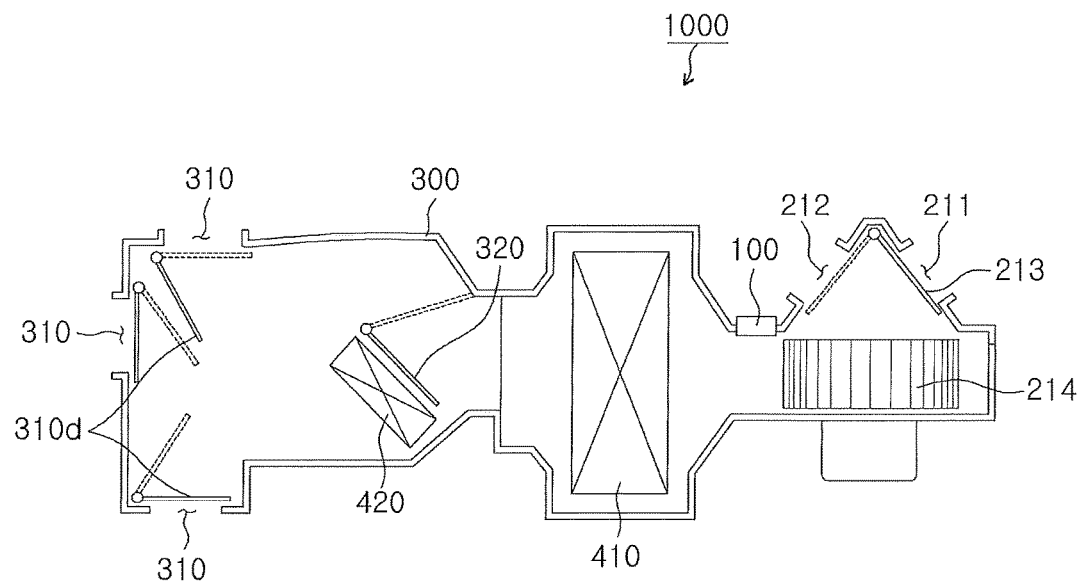
FIGS. 11 and 12 are schematic and perspective views showing an air conditioner for a vehicle having a photocatalyst device according to the present invention.
Figure 12:
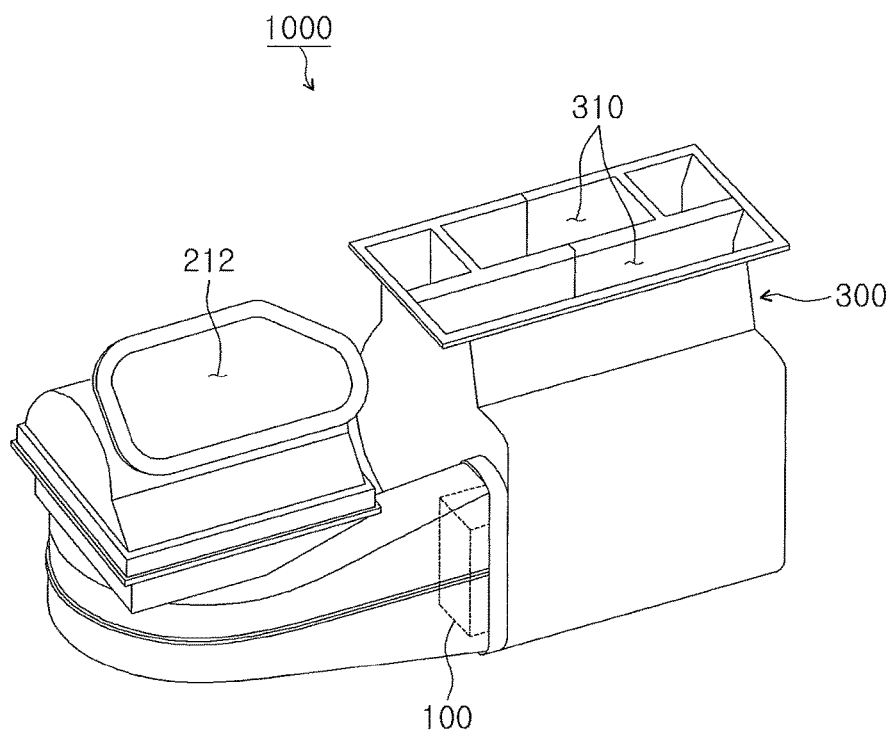

FIGS. 2 and 3 are perspective and sectional (taken along the line AA' of FIG. 2) views showing a photocatalyst device according to a first embodiment of the present invention, FIG. 4 is a perspective view showing a first radiating fin member of the photocatalyst device according to the first embodiment of the present invention, FIGS. 5 and 6 are sectional and perspective views showing a photocatalyst device according to a second embodiment of the present invention and a first radiating fin member of the photocatalyst device, FIG. 7 is a sectional view showing a photocatalyst device according to a third embodiment of the present invention, FIG. 8 is an enlarged perspective view showing a catalyst part of the photocatalyst device according to the present invention, FIGS. 9 and 10 are perspective and sectional (taken along the line BB of FIG. 9) views showing a photocatalyst device according to a fourth embodiment of the present invention, and FIGS. 11 and 12 are schematic and perspective views showing an air conditioner for a vehicle having a photocatalyst device according to the present invention.

According to the present invention, a photocatalyst device 100 largely includes a body 110, a light source part 120 and a catalyst part 130.

The body 110 supports the light source part 120 and the catalyst part 130 and has fixed portions 111 adapted to be fixed to an air conditioner case 300 of an air conditioner 1000 for a vehicle. The fixed portions 111 have a variety of shapes only if fixed to the air conditioner case 300.

Further, the body 110 includes a support portion 112, a space-forming portion 113, and a catalyst part-accommodating portion 114.

The support portion 112 serves to support a substrate 122 of the light source part 120, and the space-forming portion 113 is extended from the support portion 112 to the catalyst part 130 to form a given distance between an LED 121 of the light source part 120 and the catalyst part 130 in such a manner as to allow the light irradiated from the LED 121 of the light source part 120 to be transmitted to the catalyst part 130. At this time, the space-forming portion 113 is inclinedly increased in width as it goes from the support portion 112 toward a light irradiation direction (in a direction wherein the catalyst part 130 is located) of the light source part 120, thus guiding the light irradiated from the light source part 120 mounted on the support portion 112 to the catalyst part 130, collecting the light to the catalyst part 130, and increasing an amount of catalyst reacted. Accordingly, the number of superoxygen radicals becomes increased to enhance sterilization and deodorization effects. The catalyst part-accommodating portion 114 serves to accommodate the catalyst part 130 thereinto to guide the internal air of the air conditioner case 300 of the air conditioner 100 to the catalyst part 130. Particularly, one surface (the opposite surface to the side at which the support portion 112 is formed) of the catalyst part 130 should be exposed to the interior of the air conditioner case 300. At this time, the catalyst part-accommodating portion 114 has a stepped protrusion 114a protruding inwardly therefrom in such a manner as to support the catalyst part 130 in adjacent to the space-forming portion 113. Further, the catalyst part-accommodating portion 114 is slidingly coupled to the catalyst part 130 in such a manner as to allow the catalyst part 130 to be detachably mounted thereon, thus making it easy to perform the mounting and checking of the catalyst part 130. Of course, the catalyst part-accommodating portion 114 may have a variety of detachable coupling ways with the catalyst part 130. According to the present invention, the body 110 has a generally rectangular section, but it may have free sections like circular and other sections.

The light source part 120 is fixed to the body 110 and serves to irradiate ultraviolet light. The light source part 120 includes the LED 121 and the substrate 122 to which the LED 121 is fixed. In FIG. 4, an air flow direction is indicated by an arrow.

The LED 121 serves to irradiate UVA (Ultra Violet-A) light or UVC (Ultra Violet-C) light having a wavelength of 400 nm or under, thus solving the problems in the use of the existing mercury-vapor lamp and achieving effective light irradiation with small power. In this case, since the UVA has a relatively low price, it is advantageous in view of expense and effectively activates the photocatalytic reaction of a photocatalyst-carrying medium. Contrarily, the UVC has a relatively high price, but it performs the activation in the photocatalytic reaction and the sterilization function to improve the sterilization efficiency. Two or more light source parts 120 may be provided according to the size of the catalyst part 130. According to the present invention, if two or more light source parts 120 are provided, two or more LEDs 121 and two or more substrates 122 are provided, and otherwise, two or more LEDs 121 on one substrate 122 are provided. Of course, if two or more LEDs 121 are provided, they irradiate both of the UVA light and the UVC light.

A heat radiating part is disposed on the light source part 120 to radiate the heat generated from the light source part 120 and includes a first radiating fin member 141.

The first radiating fin member 141 serves to enhance heat radiating performance. Through the radiation of the heat generated from the LED 121 and the substrate 122, on the other hand, the light source part 120 can maintain a high light intensity. Accordingly, the first radiating fin member 141 is formed on the entire area of the light source part 120 except the area on which light is irradiated from the LED 121 to the catalyst part 130. Further, the first radiating fin member 141 has various shapes, such as a fin, plate and the like. If the first radiating fin member 141 has a shape of a plate, it is disposed on one side of the substrate 122 on which the LED 121 is located in parallel to the air flow direction.

An area to which the light is irradiated from the LED 121 to the catalyst part 130 is formed by means of the space-forming portion 113 of the body 110 between one side of the substrate 122 at which the LED 121 is located inside the body 110 and the catalyst part 130, so that the first radiating fin member 141 is located at the area to radiate the heat through the air flowing along the area. The first radiating fin member 141 as shown in FIGS. 3 and 4 does not have any protruding fins from the center area at which the LED 121 is located and has the fins inclinedly protruding downward from both sides thereof in left and right directions (air flowing direction), thus easily radiating the heat, while blocking the light irradiated from the LED 121. As shown in FIGS. 5 and 6, two LEDs 121 are located in left and right directions on the drawings, and in this case, as the first radiating fin member 141 is distant from the two LEDs 121, the fins inclinedly protrude downward. According to the present invention, the first radiating fin member 141 of the photocatalyst device 100 is not limited to the shapes as shown in the drawing, but it may be freely formed in the entire area of the light source part 120 except the area on which the light is irradiated from the LED 121 to the catalyst part 130.

According to the present invention, the photocatalyst device 100 has a second radiating fin member 142, as well, and otherwise, the substrate 122 itself serves as a heat radiating substrate, that is, a heat radiating part.

Further, the light source part 120 has the second radiating fin member 142 disposed on the opposite side to the substrate 122 on which the LED 121 is located. That is, the second radiating fin member 142 is formed on the opposite surface to the surface of the substrate 122 on which the first radiating fin member 141 and the LED 121 are located. The second radiating fin member 142 is formed on the substrate 122 or protrudes from the support portion 112 of the body 110 against which the substrate 122 is supported, thus radiating the heat generated from the light source part 120. Particularly, if the second radiating fin member 142 is formed on the substrate 122, the body 110 further includes a hollow portion 112a formed on a given area of the support portion 112 in such a manner as to allow the second radiating fin member 142 to be inserted thereinto and protrude to the outside.

The photocatalyst device 100 according to the present invention includes either of the first radiating fin member 141 or the second radiating fin member 142 or includes both of them to effectively radiate the heat generated from the LED 121, thus maintaining the high light intensity of the LED 121, enhancing high durability, and continuously keeping the sterilization and deodorization performance.

The first radiating fin member 141 and the second radiating fin member 142 come into close contact with both surfaces of the substrate 122, and they are fastened to the substrate 122 at one time through the structure for fixing the substrate 122 to the support portion 112 of the body 110.

The catalyst part 130 causes a photocatalytic reaction by the light irradiated from the light source part 120 to generate superoxygen radicals. Through the oxidation of the superoxygen radicals generated from the photocatalytic reaction, the catalyst part 130 removes the pollutants introduced into the air conditioner case 300 and eliminates the germs, all kinds of pollutants and bad odor from an evaporator 410 as will be discussed later. In more detail, if the light irradiated from the light source part 120 is absorbed to the catalyst part 130, electrons in a valence band (VB) in which the electrons are filled absorb light energy and are jumped to a conduction band (CB) in which electrons are in an empty state. The empty electron hole of the valence band oxidizes water molecules on the surface thereof and returns to its original state. The oxidized water molecules form OH radicals. Moreover, the electrons excited to the conduction band react to oxygen to produce superoxygen radicals having strong oxidizing power.

On the other hand, the catalyst part 130 includes a carrier 131 and a coating layer 132 for coating a catalyst liquefied to a form of a gel through addition of promoter and acid additive onto the carrier 131 to allow the catalyst to be carried to the carrier 131 (See FIG. 8). The carrier 131 may have a variety of shapes like a net having a plurality of pores formed at the interior thereof, and otherwise, the carrier 131 may be made of a metal or elastic material.

The catalyst includes titanium oxide $TiO_2$ having a particle size between 10 nm and 60 nm, and the surface value of the titanium oxide $TiO_2$ is more than 330 $m^2/g$. In more detail, the titanium oxide $TiO_2$ used as the photocatalyst receives the ultraviolet light of 400 nm or under to produce the superoxygen radicals, and the produced superoxygen radicals decompose organics into safe water and carbon dioxide. The titanium oxide has nano particles, so that even if the light source having the relatively weak ultraviolet wavelength intensity is used, a large number of superoxygen radicals are produced. Accordingly, the superoxygen radicals have excellent organic composing capabilities, provide continuous durability and stability even under environmental changes, and obtain semi-permanent effects. In addition, the superoxygen radicals produced in large number remove various materials like bad odor, germs and so on, as well. The catalyst part 130 is configured wherein the surface value of the titanium oxide $TiO_2$ having the nano particles is more than 330 $m^2/g$, so that when compared with normal titanium oxide, the number of particles receiving light energy on the same area as the normal titanium oxide is more raised to increase the number of superoxygen radicals produced.

At this time, the promoter is alumina, so that the carrying force of the catalyst part 130 is more improved and the fixing capability of the carrier 131 is increased.

Now, an example of a process for manufacturing the catalyst part 130 will be explained. First, titanium oxide is subjected to high-temperature plastic working and normal-temperature drying to have particle sizes between 10 nm and 60 nm and then processed to the shape of a liquid through addition of the promoter, alumina. After that, the liquid is secondarily processed according to the use purpose and carried to the carrier 131. Next, the liquid is fixed to the carrier 131 through secondary drying and plastic working.

According to the present invention, the photocatalyst device 100 has a structure wherein the superoxygen radicals are produced by the photocatalytic reaction between the light source part 120 and the catalyst part 130, so that when compared with a conventional structure wherein polluted air containing bad odor is absorbed and removed, the photocatalyst device 100 does not need any separate filter exchanging and is used almost semi-permanently through the selection in the kinds of carrier or through the appropriate on/off control of the light source part 120.

According to the present invention, as shown in FIGS. 9 and 10, the body 110 of the photocatalyst device 100 has drain holes 113a formed thereon to drain internal water therefrom. At this time, the drain holes 113a are formed on the lower side of the space-forming portion 113 in the state where the body 110 is mounted. That is, in the state where the photocatalyst device 100 is mounted on the air conditioner case 300 of the air conditioner 1000 for the vehicle, the drain holes 113a are formed on the space-forming portion 113, so that the water is guided to the drain holes 113a through the space-forming portion 113 to enhance water discharge effects.

On the other hand, the air conditioner 1000 for the vehicle according to the present invention includes the air conditioner case 300, the evaporator 410, a heater core 420 and the photocatalyst device 100.

The air conditioner case 300 conveys the air introduced thereinto, forms a space in which the evaporator 410 and the heater core 420 are mounted, and has vents 310 from which air is discharged. In more detail, the vents 310 of the air conditioner case 300 are formed to discharge the air whose temperature is adjusted by means of the evaporator 410 and the heater core 420 to the interior of the vehicle. The vents 310 includes a face vent, defrost vents, and a floor vent. The face vent 310 is a portion for discharging air to the front side (front seats) of the interior of the vehicle, the defrost vents 310 for discharging air to the windows of the interior of the vehicle, and the floor vent 310 for discharging the bottom of the front seats of the interior of the vehicle. The opening degrees of the face vent 310, the defrost vents 310 and the floor vent 310 are adjusted by means of respective mode doors 310d.

A fan 214 is disposed at the side into which the air of the air conditioner case 300 is introduced so as to blow the air, and an internal air inlet 211 and an external air inlet 212 are selectively open and closed by means of an internal and external air switching door 213, so that if the fan 214 operates, the internal air or the external air is conveyed to the air conditioner case 300. In more detail, the internal air inlet 211 communicates with the interior of the vehicle to introduce the internal air thereinto, and the external air inlet 212 with the exterior of the vehicle to introduce the external air thereinto. The internal and external air switching door 213 serves to open and close the internal air inlet 211 and the external air inlet 212. The internal and external air switching door 213 operates according to the setting of the passenger of the vehicle to selectively introduce the external air or the internal air into the interior of the vehicle.

The evaporator 410 cools air through the flow of cool refrigerant, and the heater core 420 heats air through the flow of the heated cooling water. The evaporator 410 and the heater core 420 are sequentially disposed in the air-flow direction. Further, the air conditioner case 300 has a temperature control door 320 disposed at the inside thereof to determine a degree of passing of the air passing through the evaporator 410 through the heater core 420. That is, the temperature control door 320 controls the opening degree of a hot air passage, along which the total amount of the air passing through the evaporator 410 passes through the heater core 420, and the opening degree of a cool air passage, along which the total amount of the air passing through the evaporator 410 does not pass through the heater core 420.

At this time, the photocatalyst device 100 has the above-mentioned features and is located in front of the evaporator 410 so as to sterilize and deodorize the evaporator 410.

According to the air conditioner 100 for the vehicle, further, the photocatalyst device 100 is mounted on one side of the air conditioner case 300, so that it can be easily detachably mounted on the air conditioner 1000, thus conducting easy checking and repair and minimizing the interference in the air flow in the interior of the air conditioner case 300 caused by the photo catalyst device 100. So as to fix the photocatalyst device 100 to the air conditioner case 300, particularly, the air conditioner case 300 has mounting holes 300a hollowed at given areas thereof in such a manner as to be closed by the body 110, and the body 110 of the photocatalyst device 100 has the fixed portions 111.

As shown in FIG. 10, the fixed portions 111 are hollowed on given areas thereof and have screw threads formed along the hollowed inner peripheral surfaces thereof. The mounting holes 300a of the air conditioner case 300 are hollowed correspondingly to the fixed portions 111 and have screw threads formed along the hollowed inner peripheral surfaces thereof. Accordingly, the air conditioner case 300 is fixed to the photocatalyst device 100 by means of separate fastening means 500.

At this time, each fixed portion 111 desirably protrudes from the side of the space-forming portion 113 on which the support portion 112 is formed. That is, the catalyst part 130 is located at the inside of the air conditioner case 300 and the space-forming portion 113 at the outside of the air conditioner case 300 with respect to the external surface of the air conditioner case 300. Accordingly, the catalyst part 130 is located inside the air conditioner case 300, thus effectively purifying the air, minimizing the protruding degree from the air conditioner case 300, and preventing the interference in the air flow. Further, the space-forming portion 113 is located at the outside of the air conditioner case 300 with respect to the external surface of the air conditioner case 300, thus allowing the water inside the photocatalyst device 100 to be easily discharged through the drain holes 113a formed on the space-forming portion 113 (the left side of FIG. 10 indicates the exterior of the air conditioner case 300 and the right side thereof indicates the interior of the air conditioner case 300).

As described above, the photocatalyst device and the air conditioner for a vehicle having the same purifies the air introduced into the air conditioner case, sterilizes and deodorizes the evaporator, and effectively radiates the heat generated from the photocatalyst device, thus continuously keeping the sterilization and deodorization performance.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A photocatalyst device comprising:
    a body;
    a first light source part including a substrate and an LED coupled to the substrate, the first light source part configured to irradiate ultraviolet light;
    a catalyst part coupled to the body, the catalyst part configured to conduct a photocatalytic reaction with the ultraviolet light irradiated by the first light source part to generate a plurality of superoxygen radicals; and
    a heat radiating part disposed on the first light source part, the heat radiating part configured to radiate the heat generated by the first light source part, wherein the heat radiating part includes a first radiating fin member disposed on a first side of the substrate, the first radiating fin member extending from the substrate in a direction toward the catalyst part.

2. The photocatalyst device according to claim 1, wherein the first radiating fin member is a substantially planar plate arranged to extend in parallel to a direction of an air flow encountering the first radiating fin member.

3. The photocatalyst device according to claim 1, wherein the heat radiating part further includes a second radiating fin member disposed on a second side of the substrate formed opposite the first side thereof, the first side of the substrate having the LED of the first light source disposed thereon.

4. The photocatalyst device according to claim 1, wherein the body comprises:
   a support portion configured to support the substrate of the first light source part;
   a catalyst part-accommodating portion, the catalyst part coupled to the catalyst part-accommodating portion; and
   a space-forming portion extending between the support portion and the catalyst part-accommodating portion to space the LED of the first light source part from the catalyst part.

5. The photocatalyst device according to claim 4, wherein the space-forming portion is inclinedly increased in width as the space-forming portion extends from the support portion toward the catalyst part-accommodating portion.

6. The photocatalyst device according to claim 1, wherein the body includes a drain hole therein.

7. The photocatalyst device according to claim 1, wherein the substrate includes a first surface in facing relationship with the catalyst part, the first surface coated with a waterproofing material.

8. The photocatalyst device according to claim 1, wherein the catalyst part includes a carrier and a coating layer, the coating layer formed from a portion of the catalyst liquefied to a form of a gel through addition of promoter and acid additive onto the carrier, the coating layer configured to couple the catalyst to the carrier.

9. The photocatalyst device according to claim 8, wherein the catalyst comprises titanium oxide having a particle size between 10 nm and 60 nm and a surface value of the titanium oxide is more than 330 m$^2$/g.

10. The photocatalyst device according to claim 8, wherein the promoter is alumina.

11. The photocatalyst device according to claim 1, wherein the substrate of the first light source part is configured to radiate heat.

12. The photocatalyst device according to claim 1, further including a second light source part configured to irradiate ultraviolet light, the second light source part spaced apart from the LED of the first light source part.

* * * * *